United States Patent
Smith et al.

(10) Patent No.: US 7,176,329 B2
(45) Date of Patent: Feb. 13, 2007

(54) MONOCARBOXYLIC ACID ESTERS OF PROPOXYLATED FATTY ALCOHOLS AS PIGMENT DISPERSANTS

(75) Inventors: Ronald J. Smith, Woodcliff Lake, NJ (US); Maria K. Smith, Woodcliff Lake, NJ (US); Sayer B. Needelmann, Monroe Township, NJ (US); G. Frank DeMonico, South River, NJ (US)

(73) Assignees: Innovachem, Inc., Northvale, NJ (US); Trivent Chemical Co., Inc., Monmouth Junction, NJ (US)

( * ) Notice: Subject to any disclaimer, the term of this patent is extended or adjusted under 35 U.S.C. 154(b) by 336 days.

(21) Appl. No.: 10/843,061

(22) Filed: May 11, 2004

(65) Prior Publication Data
US 2004/0210077 A1   Oct. 21, 2004

Related U.S. Application Data

(63) Continuation-in-part of application No. 10/083,631, filed on Feb. 26, 2002, now Pat. No. 6,737,543.

(60) Provisional application No. 60/273,073, filed on Mar. 2, 2001.

(51) Int. Cl.
C07C 67/02   (2006.01)

(52) U.S. Cl. .................................... 560/263

(58) Field of Classification Search ............... 560/19, 560/103, 104, 105, 129, 155, 179, 263
See application file for complete search history.

(56) References Cited

U.S. PATENT DOCUMENTS

| | | |
|---|---|---|
| 2,840,594 A | 6/1958 | Coates et al. |
| 4,323,693 A | 4/1982 | Scala, Jr. |
| 4,323,694 A | 4/1982 | Scala, Jr. |
| 4,365,084 A | 12/1982 | Young |
| 4,431,837 A | 2/1984 | Geria |
| 4,559,226 A | 12/1985 | Fogel et al. |
| 4,791,097 A | 12/1988 | Walele et al. |
| 5,116,604 A | 5/1992 | Fogel |
| 5,476,643 A | 12/1995 | Fogel |
| 5,716,602 A | 2/1998 | Uick |
| 5,928,631 A | 7/1999 | Lucas et al. |
| 2006/0165640 A1* | 7/2006 | Lebre et al. ............. 424/70.22 |

* cited by examiner

Primary Examiner—Thurman K. Page
Assistant Examiner—Karl J. Puttlitz
(74) Attorney, Agent, or Firm—Michael E. Zall

(57) ABSTRACT

A novel fatty polypropoxylate ester which is an ester of an aliphatic or an aromatic monoacid formed by reacting the acid with a stoichiometric excess of a polypropoxylated fatty alcohol. The compounds have the following structural formula:

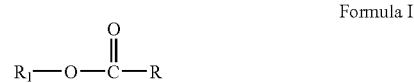

Formula I wherein $R_1$ has the structural formula:

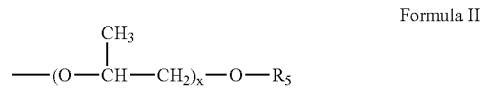

Formula II wherein $R_5$ is a saturated or unsaturated, substituted or unsubstituted aliphatic or aromatic moiety containing from 4 to 24 carbon atoms, and x is an integer from 3 to 30; and wherein R has the structural formula:

a)

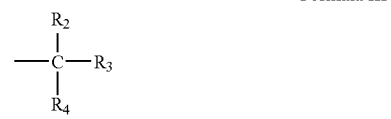

Formula III wherein $R_2$, $R_3$ and $R_4$ are independently selected from the group consisting of methyl, ethyl, propyl or isopropyl; or b)

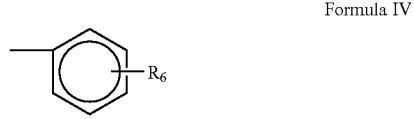

Formula IV wherein $R_6$ is H or OH or $NH_2$ or methyl or ethyl.

The compounds possess exceptional pigment dispersant and esthetic emollient properties for use in personal care and topical pharmaceutical preparations, e.g., lipsticks, cream foundations, waterproof sunscreens, sunscreen lotions.

6 Claims, No Drawings

MONOCARBOXYLIC ACID ESTERS OF PROPOXYLATED FATTY ALCOHOLS AS PIGMENT DISPERSANTS

RELATED APPLICATIONS

This application is a continuation-in-part of U.S. Ser. No. 10/083,631 filed on Feb. 26, 2002, issued as U.S. Pat. No. 6,737,543, which claims the benefit of provisional application U.S. Ser. No. 60/273,073 filed Mar. 2, 2001. The entire disclosures of these applications are incorporated herein by reference.

BACKGROUND OF THE INVENTION

1. Field of the Invention

The present invention relates to fatty polypropoxylate esters of aliphatic and aromatic monocarboxylic fatty acids. These compounds have unique pigment dispersion and emolliency properties. The fatty polypropoxylate esters of the present invention are particularly useful in the formulation of sunscreen lotions, sunscreen sprays, self-tanning compositions, make-ups and other pigmented products, cold creams, lotions, skin moisturizers, antiperspirants, after shaves, pre-electric shaves, topical pharmaceutical products, lipsticks and cleansing creams. The present invention further relates to topical preparations incorporating the fatty polypropoxylate esters of the present invention.

2. Prior Art

There has been an increased awareness among the public of the potential for skin damage from ultraviolet radiation, with frequent news reports of greater risk from sun-induced photo aging, melanoma, and other skin disorders. The contribution of UVA radiation as well as the widely recognized contribution of UVB radiation to skin damage has engendered the development of a broad range of sunscreen products from the cosmetic industry. Sophisticated sunscreen formulations have been developed which incorporate combinations of UVA and UVB absorbers in vehicles which provide wash-off resistance and enhanced esthetics. Because of the regulatory limitations on the levels at which organic sunscreens may be used in formulations and the desirability for high absorbency formulations (high SPF) with broad spectrum protection, the use of physical sunscreens in conjunction with organic sunscreens in formulations has increased greatly.

Physical sunscreens consist of very finely divided (micronized) inorganic metallic oxides, typically Titanium Dioxide or Zinc Oxide. These micronized physical sunscreens appear transparent on the skin by virtue of their small particle size. Similar to other finely divided particulate products used in cosmetic formulations such as pigments for foundations and makeups, micronized Zinc Oxide and micronized Titanium Dioxide are dispersed within the formulation by mixing, using either low-shear or high-shear methods. In order to make stable, cosmetically acceptable products, uniform dispersions must be produced, with all particles wetted out and which remain in suspension over a period of time without settling, gelling or agglomerating. Producing such stable suspensions has proved to be a challenge, although some successes have been achieved.

For example, U.S. Pat. No. 5,116,604 to Fogel describes the use of neopentanoate esters, in particular isoarachidyl neopentanoate, as cosmetic emollients for sunscreen products. U.S. Pat. No. 5,716,602 to Uick describes sunscreens formulated to include a water resistance agent and an insect repellent. One form has in an aqueous emulsion DEET, a sunscreen agent, an anionic surfactant, an alkylated PVP, and octyldodecyl neopentanoate. Both of these inventions use of Elefac I-205, i.e., Octyldodecyl Neopentanoate.

U.S. Pat. No. 5,476,643 to Fogel describes the use of two specific neopentyl glycol diesters, as wetting, dispersing, spreading and deterging agents for micronized $TiO_2$, ZnO and other pigments. These esters, neopentyl glycol di-2-ethyl hexanoate and neopentyl glycol di-isostearate, are used in varying combinations and may also be used with an emulsifying agent for a water dispersible pigmented make-up cleaner composition.

Emollients such as Finsolv TN ($C_{12}$–$C_{15}$ Alkyl Benzoate) and TRIVENT NP-13 (Tridecyl Neopentanoate) have also been employed with some success as dispersants for physical sunscreens, as have various glycols and propoxylates, such as PPG-3 Myristyl Ether. See for example, U.S. Pat. No. 5,928,631 to Lucas which describes a skin composition for controlling environmental malodors on the body. The composition comprises from about 0.1% to about 5%, by weight of a solubilized, water-soluble, uncomplexed cyclodextrin; from about 0.1% to about 36%, by weight of an oil phase selected from the group consisting of emollients, moisturizers, and skin protectants; one or more surfactants, and an aqueous carrier.

U.S. Pat. No. 4,559,226 to Fogel describes self-emulsifying alkoxylate esters useful in cosmetic compositions having a structural formula:

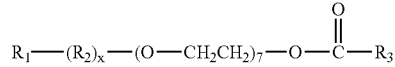

Wherein $R_1$ contains from 2 to 20 carbon atoms and is selected from the group consisting of aliphatic and aromatic substituents and $R_3$ is an alkyl or aryl substituent from 1 to 21 carbon atoms. One of $R_1$ and $R_3$ must contain greater than 8 carbon atoms.

$R_2$ is:

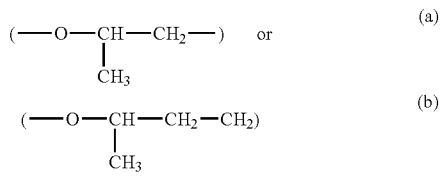

Wherein x is from 1 to 10 and y is from 1 to 20 and the ratio of y to x is from 2:1 to 10:1. Such esters are both ethoxylated and propoxylated.

Thus there remains a need for superior dispersants with desirable esthetic properties for use in pigmented cosmetic compositions, particularly sunscreen formulations that contain physical sunscreens.

Additionally, since formulators often find it useful to fully disperse pigments, e.g., micronized metallic oxides, in a portion of the oil phase by high shear techniques such as milling, there is a need for forming oil phase dispersions which have a high solids content of pigments, particularly micronized metallic oxides, that are fluid

OBJECTS AND SUMMARY OF THE INVENTION

It is a broad object of the present invention to provide a class of agents with superior dispersant properties suitable for use in the formulation of topical personal care products.

It is another object of this invention to provide compounds which are superior dispersants and have desirable esthetic properties for use in pigmented cosmetic compositions.

It is a further object of this invention to provide compounds which are superior dispersants, and have desirable esthetic properties for use in sunscreen formulations containing physical sunscreens.

It is yet another object of this invention to provide a dispersant that is useful for formulating by high shear techniques, such as milling, oil phase dispersions that have a high solids content of pigments and micronized metallic oxides.

It is a more specific object of this invention to provide dispersing agents having improved dispersant properties that are polypropoxylated fatty alcohol chains covalently bonded by ester linkages to aliphatic and aromatic monocarboxylic acids.

The aforedescribed objects and others are achieved through the present invention. Broadly, the invention is directed to certain aliphatic and aromatic monocarboxylic acid esters of polypropoxylated fatty alcohols. These compounds demonstrate unusual and unexpectedly superior properties as pigment dispersants, especially for micronized Zinc Oxide, e.g., Z-Cote HP-1 from BASF, micronized Titanium Dioxide, and uncoated pigments such as those used in foundations and makeup products. Additionally, these propoxylated alcohol esters can be used to produce uniform milled dispersions of pigments and micronized metallic oxide sunscreens that have exceptionally high solids content, exhibit unusual fluidity and when applied to the skin demonstrate a dry, elegant emolliency.

Generally, the fatty polypropoxylated esters of this invention are esters of an aliphatic or an aromatic monoacid formed by reacting an acid with a stoichiometric excess of a polypropoxylated fatty alcohol.

Broadly, the compounds of this invention have the following structural formula:

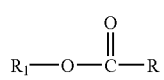

Formula I wherein $R_1$ is a polypropoxylated fatty alcohol and has the structural formula:

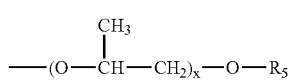

Formula II wherein $R_5$ is a saturated or unsaturated, substituted or unsubstituted aliphatic or aromatic moiety containing from 4 to 24 carbon atoms, and x is an integer from 3 to 30; and wherein R, which is derived from an aliphatic or aromatic monocarboxylic acid, has the structural formula:

a)

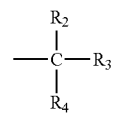

Formula III wherein $R_2$, $R_3$ and $R_4$ are independently selected from the group consisting of methyl, ethyl, propyl or isopropyl; or b)

Formula IV wherein $R_6$ is H or OH or $NH_2$ or methyl or ethyl.

A preferred group of compounds have the following structural formula:

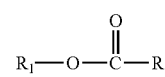

Formula I wherein $R_1$, which may be derived from a polypropoxylated fatty alcohol, has the structural formula:

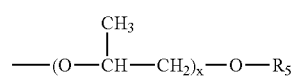

Formula II wherein $R_5$ is a straight-chain or branched-chain saturated aliphatic moiety containing from 4 to 24 carbon atoms, an aromatic moiety containing 7 or 8 carbon atoms, or an unsaturated moiety containing 14 to 18 carbon atoms and containing 1, 2 or 3 double bonds, and x is an integer from 3 to 30; and wherein R, which may be derived from an aliphatic or aromatic monocarboxylic acid, has the structural formula:

a)

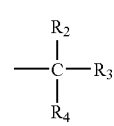

Formula III wherein $R_2$, $R_3$ and $R_4$ are independently selected from the group consisting of methyl, ethyl, propyl or isopropyl.

These compounds, for example, may be derived from tert-butanol, n-octanol, n-hexadecanol (cetyl alcohol), octyldodecanol, benzyl alcohol, phenylethyl alcohol, oleyl alcohol or linoleyl alcohol.

The present invention provides fatty polypropoxylate esters possessing exceptional pigment dispersant and esthetic emollient properties long sought by formulators for use in personal care and topical pharmaceutical preparations.

In accordance with another aspect of the present invention, there are provided compositions for topical application that include such the fatty polypropoxylate esters.

DESCRIPTION OF THE PREFERRED EMBODIMENTS

The emollient dispersants of the present invention are fatty polypropoxylate esters of aliphatic and aromatic monocarboxylic acids.

The aliphatic monocarboxylic acids suitable for preparing the compounds of the present invention contain from 2 to 24 carbon atoms. The aromatic monocarboxylic acids suitable for preparing the compounds of the present invention contain from 7 to 9 carbon atoms. Preferred aliphatic monocarboxylic acids contain from 4 to 18 carbon atoms. Examples of suitable aliphatic monocarboxylic acids include 2-Ethyl Hexanoic acid, Caproic acid, Neopentanoic acid, Isostearic acid, Neoheptanoic acid and Oleic acid. Examples of suitable aromatic moncarboxylic acids include Benzoic acid and p-Aminobenzoic acid.

The fatty polypropoxylate esters of the present invention are formed by reacting the above described aliphatic and aromatic monocarboxylic acids with polypropoxylated fatty alcohols. The polypropoxylated fatty alcohols preferably have between 3 and 30 moles of propoxylation, and most preferably between 3 and 10 moles of propoxylation. The fatty alcohols utilized to prepare these polypropoxylated fatty alcohols may be saturated or unsaturated, substituted or unsubstituted, aliphatic or aromatic, and may be straight chained or branched chained, having between 6 and 24 carbon atoms. Saturated aliphatic fatty alcohols, either straight chain or branched chain, with 12 to 14 carbon atoms are most preferred.

The fatty polypropoxylated esters of the present invention are particularly useful as agents that confer superior pigment dispersion and unusual, dry, elegant emollient properties to topical formulations, especially to those containing physical sunscreens and other pigments. The fatty polypropoxylated esters of the present invention are also singularly useful in the preparation of fluid, high solids content dispersion grinds of micronized physical sunscreens such as Zinc Oxide and Titanium Dioxide for use in sunscreen formulations. The esters are useful in the formulation of sunscreen lotions, sunscreen sprays, self-tanning compositions, make-ups and other pigmented products, cold creams, skin moisturizers, antiperspirants, after shaves, pre-electric shaves, topical pharmaceutical products, lipsticks and cleansing creams. The dry, elegant emolliency imparted by the fatty polypropoxylated esters of the present invention is manifested primarily when the esters are utilized as a full or partial replacement for the mineral oil and petrolatum emollient agents of the prior art. A distinct improvement in the esthetics and emollient properties of mineral oil and petrolatum-based products is discernible when as little as 25% of the mineral oil or petrolatum has been replaced by the fatty polypropoxylated esters of the present invention. Therefore, topical preparations in accordance with the present invention can include a second emollient agent of mineral oil, petrolatum and the like along with the fatty polypropoxylated esters of the present invention in a ratio of up to about 3:1 of the second emollient agent to the emollient agent of the present invention. These topical formulations include the essential compounds of the present invention, one or more active ingredients and water. As mentioned above, a second emollient agent of mineral oil, petrolatum and the like may be included as desired. Suitable active ingredients for use in topical preparations include organic sunscreens, physical sunscreens, self-tanning agents, pigments, opacifying agents, moisturizers, film-formers, thickening agents, emulsifiers, antiseptic agents, conditioning agents and deodorant actives.

The topical preparations of the present invention, in addition to including the primary components of the fatty polypropoxylated esters of the present invention, one or more active ingredients, water and the optional second emollient agent, may also include fragrances, humectants, protein derivatives, coloring agents, preservatives and the like.

Typical topical formulations in accordance with the present invention include the essential fatty polypropoxylated esters of the present invention either alone or in combination with the second emollient agent, in a range of from about 0.2% to about 40.0% by weight of the composition, preferably from about 2.0% to about 20.0% of the composition. As noted above, the second emollient agent, when present, may be blended with the fatty polypropoxylate ester emollients of the present invention in a ratio of about 3:1 of the former to the latter.

The topical preparations of the present invention are formulated using techniques that are well known to practitioners in the cosmetic formulating art. Typically, the ingredients are combined with mixing and the application of heat as necessary until a homogeneous product is obtained. The water soluble ingredients and water-insoluble ingredients are mixed together separately and combined with suitable emulsifying agents.

The topical compositions of the present invention are topically applied directly to the skin. The compositions can be delivered by placing the composition into a dispensing means and applying an effective amount via spraying or rubbing the composition onto the desired skin surface, either the entire body or selected portions thereof. Preferably the dispensing means is a wipe or a spray dispenser. Distribution of the composition of the present invention can also be achieved by using a pre-formed applicator such as a roller, pad, sponge, tissue, cotton ball, hand, etc. Alternatively, the user may combine the composition of the present invention with a wipe substance of his or her own choosing. To do this, the user simply chooses a wipe substance such as a commercial paper towel, tissue, sponge, cotton, pad, washcloth, or the like; and pours, from a bottle or other suitable container, a solution of the composition of the present invention over the chosen wipe substance and applies the composition to the desired area of the body. In this manner, the user may use as much or as little of the composition of the present invention as he/she desires, depending upon their intended use.

The following examples set forth below are intended to illustrate certain aspects of the present invention, and are not to be considered limiting as to the scope and nature of the present invention.

EXAMPLES

Preparation of Compounds

The fatty alcohol, e.g., Myristyl alcohol, was reacted with Propylene Oxide in the presence of alkaline catalysts in the conventional fashion, followed by neutralization with a suitable acid such as Phosphoric Acid. The resultant polypropoxylated fatty alcohol was reacted in the conventional fashion with a stoichiometric amount of the aliphatic or aromatic fatty acid, e.g., Ethylhexanoic acid, followed by neutralization with a suitable base such as Sodium Carbonate. The typical reaction is as follows:

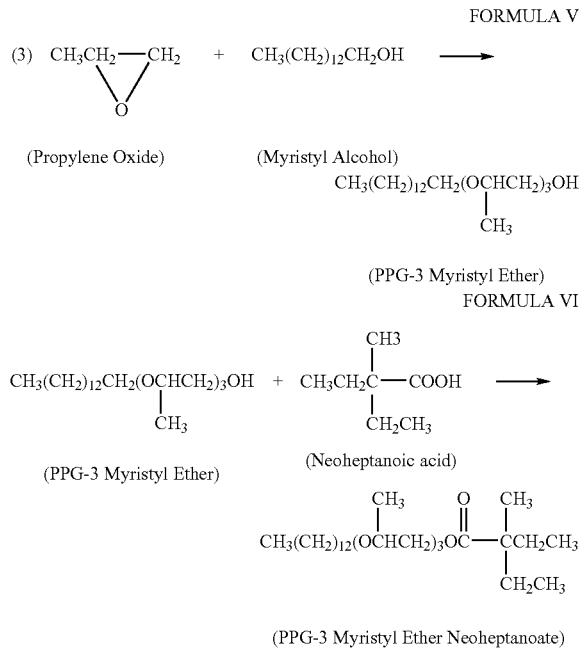

Preparation of PPG-3 Myristyl Ether Neoheptanoate 3 moles (642 grams) of Myristyl Alcohol were charged to an autoclave, and 0.1% of Potassium Hydroxide was added as a catalyst. The autoclave was purged with Nitrogen and 9 moles (522 grams) of Propylene oxide were added at a temperature of 150–160° C. and a pressure of 30–40 psi. At the completion of the addition reaction, the batch was cooled to 80° C. and neutralized with Phosphoric Acid. The resultant 1,164 grams of product, PPG-3 Myristyl Ether, a pale yellow liquid, was charged to a four-neck flask. 3 moles (390 grams) of Neoheptanoic Acid were charged to the flask, along with a catalytic amount of methanesulfonic acid. The reaction mixture was heated with agitation to 190° C. until an acid value of less than 8 mg KOH was obtained. The reaction mixture was cooled to 80° C., washed with a dilute Sodium Carbonate solution sufficient to neutralize the residual acid present, followed by washing with water. The ester layer was separated and heated under vacuum until a moisture content of less than 0.3% was obtained, followed by vacuum filtration. The resultant product, PPG-3 Myristyl Ether Neopentanoate, was a clear pale yellow liquid having an acid value of 0.12 mg KOH.

Preparation of PPG-4 Butyloctyl Ether Ethylhexanoate 4 moles (744 grams) of Butyloctanol were charged to an autoclave, and 0.1% of Potassium Hydroxide was added as catalyst. The autoclave was purged with Nitrogen and 16 moles (928 grams) of Propylene Oxide were added at a temperature of 150–160° C. and a pressure of 30–40 psi. Upon completion, the batch was cooled to 80° C. and neutralized with Phosphoric Acid. The resultant product, PPG-4 Butyloctyl Ether, was a very pale yellow liquid. A four-neck flask was charged with 1,224 grams of the PPG-4 Butyloctyl Ether, along with 3 moles (432 grams) of 2-Ethyl Hexanoic Acid. A catalytic amount of p-Toluenesulfonic Acid was added and the reaction mixture was heated with agitation to 160° C. until an acid value of less than 5 mg KOH was obtained. The reaction mixture was cooled to 80° C., washed with a dilute Sodium Hydroxide solution sufficient to neutralize the residual acid present, followed by washing with water. The ester layer was separated and heated under vacuum until a moisture content of less than 0.2% was obtained, followed by vacuum filtration. The resultant product, PPG-4 Butyloctyl Ether Ethylhexanoate, was a clear very pale yellow liquid having an acid value of less than 0.1 mg KOH.

PPG-4 Butyloctyl Ether Ethylhexanoate

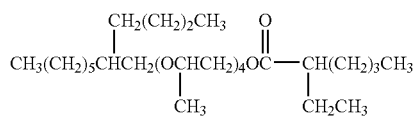

Dispersion Efficacy Testing

By use of a simple screening test for dispersant effectiveness, we have discovered that these aliphatic and aromatic esters of polypropoxylated fatty alcohols demonstrate greatly superior pigment wetting properties and greatly enhanced ability to keep physical sunscreen ingredients such as micronized Zinc Oxide in suspension. The tests show that these aliphatic and aromatic monocarboxylic acid esters of polypropoxylated fatty alcohols are superior to commonly used dispersants such as C12–C15 Alkyl Benzoate, Octyldodecyl Neopentanoate, Neopentyl Glycol Dietylhexanoate, and Tridecyl Neopentanoate, Propylene Glycol, and PPG-3 Myristyl Ether.

A dispersion of 20 grams of micronized Zinc Oxide (Z-COTE HP-1) and 80 grams of the dispersant to be tested was prepared by adding the Zinc Oxide to the test dispersant under low shear propeller agitation and mixing for 15 minutes. A 10 ml aliquot of the dispersion was then centrifuged for 10 minutes at 3500 rpm in a graduated conical centrifuge tube, and the degree of separation was noted. Using this test, dispersions were made with two of the test compounds, PPG-3 Myristyl Ether Neoheptanoate and PPG-3 Butyloctyl Ether Ethylhexanoate. These tests showed essentially no evidence of separation after centrifugation. By comparison, dispersions made with $C_{12}$–$C_{15}$ Alkyl Benzoate, Octyldodecyl Neopentanoate and Neopentyl Glycol Dietylhexanoate demonstrated approximately 30–35% separation after centrifugation, while a dispersion made with Tridecyl Neopentanoate showed an approximate 25% separation. Dispersions made with Propylene Glycol and PPG-3 Myristyl Ether demonstrated separations in excess of 50% upon centrifugation.

In other tests, 50 percent milled dispersions of micronized Titanium Dioxide (WC&D CTFA 328) were prepared in PPG-3 Myristyl Ether Neoheptanoate and in Elefac I-205 by first mixing the pigment with the vehicle until the pigment was thoroughly wetted, and then passing the resultant mixture over a three roller mill. The quality of the grind was measured using a Hegman Gauge, confirming a particle size of less than one micron for each preparation. The grind prepared using Elefac I-205 was an immobile paste, while the grind prepared using PPG-3 Myristyl Ether Neoheptanoate was a thin fluid. Using the same methodology, 50 percent milled dispersions of Ultrafine Zinc Oxide (Z-Cote, untreated) were prepared in PPG-3 Myristyl Ether Neoheptanoate and in Finsolv TN. The grind prepared using Finsolv TN was an immobile paste, while the grind prepared using PPG-3 Myristyl Ether Neoheptanoate was a thin fluid.

Cosmetic Preparations

The following examples, while not intended to be limiting, demonstrate topical preparations formulated into a lipstick, a sunscreen lotion containing micronized Titanium Dioxide, a waterproof sunscreen lotion containing micronized Zinc Oxide, and a pigmented cream foundation.

Preparation of Emollient Lipstick

| Phase | INCI Name | Percent |
|---|---|---|
| A | PPG-3 Myristyl Ether Neoheptanoate (TRIVASPERSE NH - Trivent) | 10.00 |
|   | Castor Oil | 41.35 |
| B | Red #6 (1:2 in Castor Oil) | 1.90 |
|   | Red #7 (1:1 in Castor Oil) | 2.38 |
|   | Yellow #5 (1:2 in Castor Oil) | 0.32 |
|   | Titanium Dioxide (1:1 in Castor Oil) | 1.75 |
|   | Blue #1 (0.75:2.25 in Castor Oil) | 0.10 |
| C | Mango Butter (Trivent) | 7.00 |
|   | Octyl Methoxycinnamate (Trivent OMC - Trivent) | 2.50 |
|   | Hydrogenated Polyisobutene (Panalane H-300 E - Lipo) | 5.00 |
|   | Candelilla Wax | 4.50 |
|   | White Beeswax | 4.50 |
|   | Ozokerite Wax | 5.00 |
|   | Carnauba Wax | 1.50 |
|   | Emulsifying Wax | 0.75 |
|   | Polyglyceryl-3 Methylglucose Distearate (Tego Care 450 - Goldschmidt) | 2.50 |
| D | Nylon 12 And Boron Nitride (Liponyl 10 BN 6069 - Lipo) | 8.00 |
| E | Tocopheryl Acetate | 0.10 |
|   | Wheat Germ Oil | 0.25 |
|   | Isopropylparaben, Isobutylparaben, Butylparaben (Liquipar Oil-Sutton Labs) | 0.60 |
|   | Total | 100.00 |

Disperse B into A. Heat C to 80°–85° C. and mix until melted and uniform. Heat AB to 80°–85° C. and add to C while mixing slowly. Maintain temperature and mix until uniform. Take care not to aerate batch. Mix and cool to 65° C. Add D and E. Maintain temperature, mix until uniform, then pour into molds.

Preparation of Cream Foundation

| Phase | INCI Name | Percent |
|---|---|---|
| A | Deionized Water | 35.95 |
|   | Triethanolamine, 99% | 1.85 |
|   | Glycerine, USP | 3.00 |
|   | Trisodium EDTA | 0.10 |
|   | Simethicone (Anti-Foam AF-Dow Corning) | 0.10 |
| B | Glyceryl Stearate | 3.50 |
|   | Stearic Acid | 3.00 |
|   | Laureth-2 | 31.00 |
|   | Cetyl Alcohol | 3.00 |
|   | Hydrogenated Vegetable Oil | 7.50 |
| C | PPG-3 Myristyl Ether Neoheptanoate (TRIVASPERSE NH - Trivent) | 5.00 |
|   | Dimethicone | 2.00 |
|   | Iron Oxide Red | 0.20 |
|   | Iron Oxide Yellow | 0.63 |
|   | Iron Oxide Black | 0.08 |
|   | Iron Oxide Brown | 0.09 |
|   | Titanium Dioxide | 1.00 |
|   | Talc | 1.00 |
| D | Carbomer (Carbopol 940, 2% aqueous solution - BFGoodrich) | 30.00 |

-continued

| Phase | INCI Name | Percent |
|---|---|---|
| E | Phenoxyethanol (and) Methylparaben (and) Butylparaben (and) Ethylparaben (and) Propylparaben (Phenonip - Nipa) | 1.00 |
|   | Total | 100.00 |

In main vessel, mix and heat Phase A to 65–70° C. In a separate vessel, mix and heat Phase B to 65–70° C. In an appropriately-sized vessel, mix Phase C until completely dispersed. When Phase B is at temperature, add Phase C to Phase B and mix until uniform. Begin homogenizing Phase A. Slowly add combined Phase B to Phase A while homogenizing. Homogenize for 5–10 minutes, until uniform. Switch to propeller mixer and begin cooling batch. At 55–60° C., add Phase D to main batch. Maintain minimum temperature of 50° C. Cool batch with stirring to 35–40° C. and add Phase E. Mix until uniform. Continue mixing while cooling batch to room temperature (20–25° C).

Preparation of Waterproof Sunscreen (Zinc Oxide)

| Phase | INCI Name | Percent |
|---|---|---|
| A | Polyglyceryl-4 Isostearate (and) Cetyl Dimethicone Copolyol (and) Hexyl Laurate (Abil WE-09 - Goldschmidt) | 5.00 |
|   | Cetyl Dimethicone (Abil Wax 9801 - Goldschmidt) | 1.00 |
|   | Beeswax | 0.75 |
|   | Octyl Methoxycinnamate (Trivent OMC) | 7.50 |
|   | Octyl Palmitate (Trivent OP) | 3.00 |
|   | Cetyl Acetate (and) Acetylated Lanolin Alcohols (Trivent ALA) | 2.00 |
|   | Cyclopentasiloxane | 3.00 |
|   | Cetyl Palmitate (Trivent CP) | 1.00 |
|   | Dimethicone | 0.25 |
| B | PPG-3 Myristyl Ether Neoheptanoate (TRIVASPERSE NH - Trivent) | 7.50 |
|   | Zinc Oxide (Z-Cote - BASF) | 7.50 |
| C | Deionized Water | 59.60 |
|   | Sodium Chloride | 0.80 |
|   | Trisodium EDTA | 0.10 |
| D | Phenoxyethanol (and) Methylparaben (and) Butylparaben (and) Ethylparaben (and) Propylparaben (Phenonip - Nipa) | 1.00 |
|   | Total | 100.00 |

In main vessel, mix and heat Phase A to 70° C. In an appropriately-sized vessel, mix Phase B until completely dispersed. When Phase B is dispersed, add to Phase A. In a separate vessel, mix and heat Phase C to 70° C. At temperature, add Phase C to Phase A slowly with stirring. Homogenize batch for 5–10 minutes. Switch to propeller mixer and cool batch to 45° C. At 45° C., add Phase D to batch and mix until uniform. Continue mixing and cool batch to room temperature (20–25° C.).

Preparation of Sunscreen Lotion (Titanium Dioxide)

| Phase | INCI Name | Percent |
|---|---|---|
| A | Deionized Water | 60.20 |
|   | Trisodium EDTA | 0.10 |
|   | Butylene Glycol | 2.00 |
|   | Xanthan Gum | 0.30 |
| B | Octyl Methoxycinnamate (Trivent OMC) | 7.50 |
|   | Glyceryl Stearate/PEG-100 Stearate | 1.50 |
|   | Cetyl Dimethicone (Abil Wax 9801 - Goldschmidt) | 1.00 |

-continued

| Phase | INCI Name | Percent |
|---|---|---|
|  | Pentaerythritol Tetra-2-Ethylhexanoate (Trivent PE-48) | 3.00 |
|  | Cetearyl Alcohol | 2.50 |
|  | Ceteareth-20 | 0.40 |
|  | Tocopheryl Acetate | 0.50 |
|  | Beeswax | 0.50 |
|  | Cetyl Palmitate (Trivent CP) | 1.25 |
| C | PPG-3 Myristyl Ether Neoheptanoate (TRIVASPERSE NH - Trivent) | 8.75 |
|  | Titanium Dioxide (Micro LA-20 - Grant) | 6.50 |
|  | Polysorbate-20 | 1.00 |
| D | Polyacrylamide (and) $C_{13-14}$ Isoparaffin (and) Laureth- (Sepigel 305 - Seppic) | 72.00 |
| E | Phenoxyethanol (and) Methylparaben (and) Butylparaben (and) Ethylparaben (and) Propylparaben (Phenonip - Nipa) | 1.00 |
|  | Total | 100.00 |

In main vessel, mix and heat Phase A to 65–70° C. In a separate vessel, mix and heat Phase B to 65–70° C. In an appropriately-sized vessel, mix Phase C until completely dispersed. At temperature, add Phase B to Phase A and begin homogenization. While homogenizing, add Phase C to batch. Continue homogenizing and add Phase D to batch. Homogenize for 5 minutes, until uniform. Switch to propeller mixer. Cool batch to 40–45° C. and add Phase E. Mix until uniform. Continue mixing and cool batch to room temperature (20–25° C.).

Comparative Discussion and Comparative Examples

Generally, there are substantive differences in properties between propoxylates and ethoxylates of any given reactive substrate. For example, propoxylates of fatty alcohols, fatty acids, fatty amines, and fatty amides, generally have similar properties and functionality with respect to aqueous solubility, aqueous dispersibility, physical form and surfactancy. Likewise, ethoxylates of fatty alcohols, fatty acids, fatty amines, and fatty amides, also have similar properties and functionality with respect to aqueous solubility, aqueous dispersibility, physical form and surfactancy. However, the properties and functionality of propoxylates compared to ethoxylates are generally completely different from each other. For example, whereas the propoxylates are insoluble in water, will not emulsify in water without the aid of surfactants, are oily liquids and do not function as surfactants, ethoxylates are soluble in water, are waxy solids and function as surfactants and emulsifiers.

While ethylene oxide and propylene oxide differ only by a methyl group, they nevertheless impart vastly different properties to substrates with which they are reacted. As a typical example, fatty alcohols may be derivatized by reaction with either propylene oxide or with ethylene oxide, yielding propoxylated fatty alcohols and ethoxylated fatty alcohols, respectively.

As a typical example, Cetyl Alcohol (1-hexadecanol), a fatty alcohol which is a waxy solid with a melting point of approximately 45° C., is essentially insoluble in water. For example, when Cetyl Alcohol, is reacted with 6 moles of ethylene oxide (Comparative Example 1), the resultant derivative, POE-6 Cetyl Ether, is a soft waxy solid which is completely soluble in water, and which functions both as an emulsifier and as a surfactant. In contrast thereto, when Cetyl Alcohol is reacted with 6 moles propylene oxide (Comparative Example 2), the resultant derivative, PPG-6 Cetyl Ether, is an oily liquid which is essentially insoluble in water and which does not function either as an emulsifier or a surfactant.

COMPARATIVE EXAMPLE 1

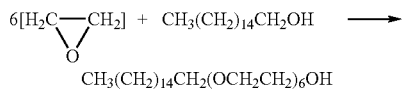

COMPARATIVE EXAMPLE 2

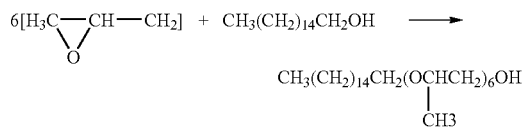

While the compound of Comparative Example 1 only differs from the compound of Comparative Example 2 by the absence of methyl groups along the polyoxypropylene chain, its properties and functions are very different.

If one were to further derivatize the compounds of Comparative Example 1 and Comparative Example 2 above by reaction with a carboxylic acid, the essential attributes of propoxylated fatty alcohols and of ethoxylated fatty alcohols are still retained. For example, the Acetic Acid ester of Comparative Example 1 above, POE-6 Cetyl Ether Acetate, is a soft waxy solid which is completely soluble in water, and which functions both as an emulsifier and as a surfactant. In contrast, the Acetic Acid ester of Comparative Example 2 above, PPG-6 Cetyl Ether Acetate, is an oily liquid which is essentially insoluble in water and which does not function either as an emulsifier or as a surfactant.

Compounds which incorporate both ethylene oxide and propylene oxide reacted with a fatty substrate, for example PPG-3 POE-3 Cetyl Ether, exhibit properties intermediate between those of Comparative Example 1 and Comparative Example 2. Typically, they tend to be dispersible in—rather than miscible with—water, and exhibit lessened emulsifier and surfactant properties versus compounds of Comparative Example 1. Carboxylic acid esters of these mixed alkoxylates also retain these intermediate properties.

With this background information, reference is made to the compounds disclosed in U.S. Pat. No. 4,559,226 to Fogel. The essence of the invention of '226 Fogel, lies in the discovery that certain carboxylic acid esters of fatty alcohols which have been both ethoxylated and propoxylated in certain defined ratios, form novel self-emulsifying emollients. These compounds were found to be particularly useful in preventing chalking in antiperspirant compositions containing volatile silicone oil. The novel functionalities and properties for the compounds disclosed in '226 Fogel (e.g., water dispersability) are directly attributable to the presence of both the ethoxylate and propoxylate substituents of the compounds.

For example, a typical compound disclosed in '226 Fogel is PPG-1 Ceteth-3 Acetate (PPG-1 POE-3 Cetyl Ether Acetate). Because this molecule incorporates both propoxylation and ethoxylation within its structure, it exhibits properties intermediate between ethoxylate esters and propoxylate esters, giving it its unique self-emulsifying characteristics. In contrast thereto, the compound of the present invention, for example, PPG-3 Myristyl Ether Neoheptanoate [which is only propoxylated, i.e., there is no ethoxylation in the structure] is essentially insoluble in water.

The compounds of the present invention do not exhibit the self-emulsifying properties of the alkoxylate esters disclosed in '226 Fogel, in that they will not disperse in water and do not function as self-emulsifiers. They do, however, exhibit their own unique properties not shared by the compounds disclosed in '226 Fogel, in that they function as exceptional pigment dispersants with unusually elegant emolliency. Their exceptional pigment dispersant properties were demonstrated in the Dispersion Efficiency tests described herein.

To demonstrate the differences between these two classes of compounds, Dispersion Efficiency tests were performed, utilizing the same protocols described herein, using PPG-1 Ceteth-3 Acetate as the test dispersant.

COMPARATIVE EXAMPLE 3

A dispersion of 20 grams of micronized Zinc Oxide (Z-COTE HP-1) and 80 grams of PPG-1 Ceteth-3 Acetate was prepared by adding the Zinc Oxide to the PPG-1 Ceteth-3 Acetate under low shear propeller agitation and mixing for 15 minutes. A 10 ml aliquot of the dispersion was then centrifuged for 10 minutes at 3,500 rpm in a graduated conical centrifuge tube, and the degree of separation was noted. Under these test conditions, the PPG-1 Ceteth-3 Acetate dispersion demonstrated a 50% separation upon centrifugation. This result was in marked contrast to this same test using PPG-3 Myristyl Ether Neoheptanoate as the dispersant, where essentially no evidence of separation following centrifugation was noted.

COMPARATIVE EXAMPLE 4

A 50 percent milled dispersion of micronized Titanium Dioxide (WC&D CTFA 328) was prepared in PPG-1 Ceteth-3 Acetate by first mixing the pigment with the vehicle until the pigment was thoroughly wetted, and then passing the resultant mixture over a three roller mill. The quality of the grind was measured using a Hegman Gauge, confirming a particle size of less than one micron for the preparation. The resultant grind was an immobile paste. This result was in marked contrast to the same test using PPG-3 Myristyl Ether Neoheptanoate, where the resultant grind was a thin fluid.

COMPARATIVE EXAMPLE 5

A 50% milled dispersion of ultrafine Zinc Oxide (Z-COTE, untreated) was prepared in PPG-1 Ceteth-3 Acetate by first mixing the pigment with the vehicle until the pigment was thoroughly wetted, and then passing the resultant mixture over a three roller mill. The quality of the grind was measured using a Hegman Gauge, confirming a particle size of less than one micron for the preparation. The resultant grind was an immobile paste. This result was in marked contrast to the same test using PPG-3 Myristyl Ether Neoheptanoate, where the resultant grind was a thin fluid.

The differences in physical properties, aqueous solubilities, and functionalities between ethoxylates, propoxylates and alkoxylates containing both ethylene oxide and propylene oxide are substantial, although they differ only in the presence or absence of methyl groups on the ether portions of the molecules. In our testing, these differences extend beyond physical appearance, surfactancy and water-dispersibility to include large differences in pigment dispersing power between the two classes of compounds.

It is understood that the embodiments described herein are merely exemplary and that a person skilled in the art may make many variations and modifications without departing from the spirit and scope of the invention. All such variations and modifications are intended to be included within the scope of the invention.

What is claimed is:

1. A topical composition for topical application comprising:
    an effective amount of an active ingredient dispersed in the topical composition, the active ingredient selected from the group consisting of pigments, micronized physical sunscreens, organic sunscreens, self-tanning agents, opacifying agents, antiseptic agents, moisturizers, film formers, deodorant actives, emulsifiers, thickening agents and conditioning agents; and
    a dispersant emollient agent in sufficient amount to disperse such active ingredient, such agent being PPG-3 Myristyl Ether Neoheptanoate.

2. The composition of claim 1, wherein the active ingredient is a pigment selected from the group consisting of Zinc Oxide or Titanium Dioxide.

3. The composition of claim 2, wherein the active ingredient is present in an amount in the range of about 0.20 to about 40.0 percent by weight of said composition.

4. A topical composition for topical application comprising:
    an effective amount of an active ingredient dispersed in the topical composition, the active ingredient selected from the group consisting of pigments, micronized physical sunscreens, organic sunscreens, self-tanning agents, opacifying agents, antiseptic agents, moisturizers, film formers, deodorant actives, emulsifiers, thickening agents and conditioning agents; and
    a dispersant emollient agent in sufficient amount to disperse such active ingredient, such agent being PPG-4 Butyloctyl Ether Ethylhexanoate.

5. The composition of claim 4, wherein the active ingredient is a pigment selected from the group consisting of Zinc Oxide or Titanium Dioxide.

6. The composition of claim 4, wherein at least one active ingredient is present in an amount in the range of about 0.20 to about 40.0 percent by weight of said composition.

* * * * *